United States Patent
Yamagata et al.

(10) Patent No.: US 6,197,350 B1
(45) Date of Patent: Mar. 6, 2001

(54) METHOD OF PRODUCING A SUSTAINED-RELEASE PREPARATION

(75) Inventors: Yutaka Yamagata, Kobe; Masafumi Misaki, Takarazuka; Susumu Iwasa, Kyotanabe, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/308,971

(22) PCT Filed: Dec. 18, 1997

(86) PCT No.: PCT/JP97/04671

§ 371 Date: May 27, 1999

§ 102(e) Date: May 27, 1999

(87) PCT Pub. No.: WO98/27980

PCT Pub. Date: Jul. 2, 1998

(30) Foreign Application Priority Data

Dec. 20, 1996 (JP) .................................................. 8-342046

(51) Int. Cl.[7] ................................ A61F 2/00; A61K 9/14; A61K 9/50
(52) U.S. Cl. .......................... 424/501; 424/426; 424/489; 424/500; 424/502
(58) Field of Search ..................................... 424/426, 408, 424/409, 489, 500, 501, 502

(56) References Cited

U.S. PATENT DOCUMENTS

| | | | | |
|---|---|---|---|---|
| 4,942,035 | * | 7/1990 | Churchill et al. | 424/423 |
| 5,874,064 | * | 2/1999 | Edwards et al. | 424/46 |

FOREIGN PATENT DOCUMENTS

| | | |
|---|---|---|
| 0 633 020 | 1/1995 | (EP) . |
| 0681 833 | 11/1995 | (EP) . |
| WO 92 00998 | 1/1992 | (WO) . |
| WO 92 17200 | 10/1992 | (WO) . |
| WO 93 13792 | 7/1993 | (WO) . |
| WO 93 17668 | 9/1993 | (WO) . |
| WO 94 12158 | 6/1994 | (WO) . |
| WO 94 19020 | 9/1994 | (WO) . |
| WO 95 29664 | 11/1995 | (WO) . |
| WO 96 07399 | 3/1996 | (WO) . |
| WO 96 40072 | 12/1996 | (WO) . |
| WO 97 03692 | 2/1997 | (WO) . |

\* cited by examiner

Primary Examiner—Thurman K. Page
Assistant Examiner—S. Tran
(74) Attorney, Agent, or Firm—Philippe Y. Riesen

(57) ABSTRACT

A method of producing sustained-release microcapsules which comprises dispersing a physiologically active polypeptide into a solution of a biodegradable polymer and zinc oxide in an organic solvent, followed by removing the organic solvent; which provides a sustained-release preparation showing a high entrapment ratio of the physiologically active polypeptide and its constant high blood concentration levels over a long period of time.

11 Claims, No Drawings

METHOD OF PRODUCING A SUSTAINED-RELEASE PREPARATION

TECHNICAL FIELD

The present invention relates to a method of producing a sustained-release preparation comprising a physiologically active polypeptide.

BACKGROUND ART

It is known that physiologically active polypeptides or their derivatives exhibit a variety of pharmacological activities in vivo. Some of these have been produced on a large scale by utilizing *Escherichia coli*, yeasts, animal cells or host animals such as goat and hamsters using recently developed genetic engineering and cell technology, and put to medicinal use. However, these physiologically active polypeptides must be frequently administered because of the generally short biological half-life. The repeated injections takes a significant physical burden on patients.

For instance, growth hormone (hereafter sometimes referred to as GH), a representative hormone which is originally produced and secreted in the anterior portion of the pituitary gland, is a physiologically active polypeptide having widely diverse physiological activities such as promotion of growth in the body, metabolism of glucose and lipids, anabolism of protein, and cell proliferation and differentiation. And GH is produced on a large scale by utilizing *Escherichia coli* using genetic recombination technology, and put to medicinal use clinically and world-widely. However, GH must be frequently administered in order to maintain an effective blood concentration because of the short biological half-life. Especially, in the case of pituitary dwarfism, a daily subcutaneous administration to infants or young patients over a long period of time ranging from a few months to at least 10 years is conducted practically.

To overcome this problem, various attempts have been made to develop a sustained-release preparation comprising a physiologically active polypeptide.

JP-A 3055/1996 (EP-A 633020) discloses a method of producing a sustained-release preparation which comprises permitting a water-soluble polypeptide to permeate into a biodegradable matrix comprising a biodegradable polymer and a metal salt of a fatty acid in an aqueous solution, and a sustained-release microcapsules (hereafter sometimes referred to as MC) prepared by this method.

JP-A 217691/1996 (WO 96/07399) discloses production of a water-insoluble or slightly water-soluble polyvalent metal salt by using a water-soluble peptide type of physiologically active substance and an aqueous solution of zinc chloride etc., and a method of producing a sustained-release preparation containing this salt and a biodegradable polymer.

WO 94/12158 discloses addition of a polymer erosion rate modulating agent such as zinc hydroxide in an amount of 0.1 to 30% (w/w) relative to the polymer to a polymer solution, as a method of producing a sustained-release preparation comprising human GH and biodegradable polymer. This publication further discloses a method of producing MC as porous particles by spraying a solution of human GH and a polymer in an organic solvent into liquid nitrogen with biological activity retained.

WO 92/17200 and Nature Medicine, Vol. 2, p. 795 (1996) disclose a method of producing a sustained-release preparation by using a zinc salt of human GH.

WO 95/29664 discloses a method of producing MC which comprises the steps of dispersing a metal salt such as zinc carbonate in a solid state in a polymer solution, adding a physiologically active substance such as hormones, and dispersing the physiologically active substance and a metal cation component separately through a biodegradable polymer.

Although, as described above, various attempts have been made to produce a sustained-release preparation with a physiological activity of a physiologically active polypeptide retained, a clinically satisfying preparation has not been obtained yet since some physiologically active polypeptides have problems such as a low entrapment ratio of the physiologically active polypeptide in the preparation, an excess release at an initial stage after administration, an unattained constant release over a long period of time, and an unretained satisfying blood concentration over a long period of time. Further, production methods, in many cases, are not suitable for industrialization which premises a large-scale production in the present situation.

DISCLOSURE OF INVENTION

Through intensive investigation to resolve the above problems, the present inventors found that co-presence of lactic acid/glycolic acid copolymer (hereafter sometimes referred to as PLGA) used as a MC base and zinc oxide in an organic solvent unexpectedly provides dissolution of zinc oxide which itself is insoluble in an organic solvent, and yields PLGA-zinc oxide complex efficiently in high contents, and that a direct dispersion of a physiologically active polypeptide in a solution of the PLGA-zinc oxide complex in an organic solvent and subsequent molding yields a sustained-release preparation having excellent properties such as an enhanced entrapment ratio of the physiologically active polypeptide, a reduced initial burst after administration, and an excellent sustained-release. Further, the present inventors found that this production method has reduced a number of steps and is a quite suitable method for industrialization. After further investigations, the present inventors developed the present invention.

Namely, the present invention relates to (1) a method of producing a sustained-release preparation which comprises dispersing a physiologically active polypeptide into a solution of a biodegradable polymer and zinc oxide in an organic solvent, followed by removing the organic solvent;

(2) the method according to the above (1), wherein the physiologically active polypeptide is growth hormone;

(3) the method according to the above (1), wherein the biodegradable polymer is lactic acid/glycolic acid copolymer;

(4) the method according to the above (3), wherein a molecular composition ratio of lactic acid/glycolic acid in the lactic acid/glycolic acid copolymer is about 85/15 to about 50/50;

(5) the method according to the above (3), wherein the weight-average molecular weight of the lactic acid/glycolic acid copolymer is about 8,000 to about 20,000;

(6) the method according to the above (1), wherein the content of zinc relative to the biodegradable polymer in the organic solvent solution is about 0.001 to about 2% by weight;

(7) the method according to the above (1), wherein the mean particle diameter of the sustained-release preparation is about 0.1 to about 300 μm;

(8) the method according to the above (1), wherein the sustained-release preparation is for injection;

(9) the method according to the above (1), wherein an o/w emulsion comprising a dispersion prepared by dispersing growth hormone into a solution of lactic acid/glycolic acid copolymer and zinc oxide in an organic solvent as an oil phase is subjected to in-water drying;

(10) the method according to the above (1), wherein the preparation is a microcapsule;

(11) a solution of lactic acid/glycolic acid copolymer and zinc oxide in an organic solvent;

(12) a lactic acid/glycolic acid copolymer-zinc oxide complex which is soluble in an organic solvent and which is obtained by co-presence of lactic acid/glycolic acid copolymer and zinc oxide in an organic solvent;

(13) a dispersion which is prepared by dispersing a physiologically active polypeptide into a solution of lactic acid/glycolic acid copolymer and zinc oxide in an organic solvent;

(14) the dispersion according to the above (13), wherein the physiologically active polypeptide is growth hormone; and

(15) the sustained-release preparation which is produced by the method according to the above (1).

Preferable examples of the biodegradable polymers used in the present invention include polymers synthesized from one or more α-hydroxycarboxylic acids (e.g., glycolic acid, lactic acid), hydroxydicarboxylic acids (e.g., malic acid), hydroxytricarboxylic acids (e.g., citric acid) etc. by catalyst-free dehydration condensation polymerization and having a free terminal carboxyl group, mixtures thereof, poly-α-cyanoacrylates, polyamino acids (e.g., poly-γ-benzyl-L-glutamic acid) and maleic anhydride copolymers (e.g., styrene-maleic acid copolymers).

Polymerization may be of the random, block or graft type. When the above-mentioned α-hydroxycarboxylic acids, hydroxydicarboxylic acids and hydroxytricarboxylic acids have an optical active center in their molecular structures, they may be of the D-, L- or DL-configuration.

Among these polymers, a biodegradable polymer having a free terminal carboxyl group such as polymers synthesized from α-hydroxycarboxylic acids (e.g., glycolic acid, lactic acid) (e.g., lactic acid/glycolic acid copolymer) and poly-α-cyanoacrylates are preferred. The biodegradable polymer is more preferably a polymer synthesized from α-hydroxycarboxylic acids, especially preferably lactic acid/glycolic acid copolymer.

When the biodegradable polymer used is a lactic acid/glycolic acid copolymer or homopolymer, its composition ratio (mol %) is preferably about 100/0 to about 40/60, more preferably about 85/15 to about 50/50.

In the present specification, lactic acid/glycolic acid copolymer as well as homopolymers such as polylactic acid and polyglycolic acid is sometimes simply referred to as lactic acid/glycolic acid polymer.

The weight-average molecular weight of the above-described lactic acid/glycolic acid polymer is preferably about 3,000 to about 25,000, more preferably about 5,000 to about 20,000.

The degree of dispersion (weight-average molecular weight/number-average molecular weight) of the lactic acid/glycolic acid polymer is preferably about 1.2 to about 4.0, more preferably about 1.5 to about 3.5.

Regarding weight-average molecular weight and degree of dispersion, the present specification holds that the former is in terms of polystyrene as determined by gel permeation chromatography (GPC) using 9 polystyrenes as reference substances with weight-average molecular weights of 120,000, 52,000, 22,000, 9,200, 5,050, 2,950, 1,050, 580 and 162, respectively, and that the latter is calculated therefrom. The above determination was carried out using a GPC column KF804Lx2 (produced by Showa Denko, Japan) and an RI monitor L-3300 (produced by Hitachi, Ltd., Japan) with chloroform as a mobile phase.

A biodegradable polymer having a free terminal carboxyl group is a biodegradable polymer wherein the number-average molecular weight based on GPC measurement and the number-average molecular weight based on terminal group quantitation almost agree with each other.

The number-average molecular weight based on terminal group quantitation is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide while stirring at room temperature (20° C.) with phenolphthalein as an indicator to determine the carboxyl group content; the number-average molecular weight based on terminal group quantitation is calculated from the following equation:

Number-average molecular weight based on terminal group quantitation=20000×A/B

A: Weight mass (g) of biodegradable polymer
B: Amount (ml) of the 0.05 N alcoholic solution of potassium hydroxide added until titration end point is reached While the number-average molecular weight based on terminal group quantitation is an absolute value, that based on GPC measurement is a relative value that varies depending on various analytical conditions (e.g., kind of mobile phase, kind of column, reference substance, slice width chosen, baseline chosen etc.); it is therefore difficult to have an absolute numerical representation of these two values. However, the description that the number-average molecular weight based on GPC measurement and that based on terminal group quantitation almost agree means, for instance, that the number-average molecular weight based on terminal group quantitation falls within the range from about 0.5 to about 2 times, preferably from about 0.7 to about 1.5 times, of the number-average molecular weight based on GPC measurement in a polymer which is synthesized from one or more α-hydroxycarboxylic acids.

For example, in the case of a polymer having a free terminal carboxyl group and which is synthesized from one or more α-hydroxycarboxylic acids by catalyst-free dehydration condensation polymerization, the number-average molecular weight based on GPC measurement and the number-average molecular weight based on terminal group quantitation almost agree with each other. On the other hand, in the case of a polymer having substantially no free terminal carboxyl groups and which is synthesized from a cyclic dimer by ring-opening polymerization using a catalyst, the number-average molecular weight based on terminal group quantitation is significantly (about 2 times or more) higher than that based on GPC measurement. This difference makes it possible to clearly differentiate a polymer having a free terminal carboxyl group from a polymer having no free terminal carboxyl group.

A lactic acid/glycolic acid polymer having a free terminal carboxyl group can be produced by a per se known process such as that described in JP-A 28521/1986 (e.g., process by catalyst-free dehydration condensation polymerization reaction or dehydration condensation polymerization reaction in the presence of an inorganic solid acid catalyst).

The decomposition/elimination rate of a lactic acid/glycolic acid polymer varies widely, depending on composition rate or weight-average molecular weight. Drug release duration can be extended by lowering the glycolic acid ratio or increasing the molecular weight, since decomposition/ elimination is usually delayed as the glycolic acid ratio decreases. Conversely, drug release duration can be shortened by increasing the glycolic acid ratio or decreasing the molecular weight. To obtain a long-term (e.g., 1–4 months) sustained-release preparation, it is preferable to use a lactic acid/glycolic acid polymer whose composition ratio and weight-average molecular weight are within the above-described ranges.

Therefore, in the present invention, composition of a biodegradable polymer used is preferably selected according to the desired kinds of a physiologically active polypeptide and the desired duration. In a specific example, for instance, when GH is used as a physiologically active polypeptide, lactic acid/glycolic acid copolymer is preferably used. In the lactic acid/glycolic acid copolymer, lactic acid/glycolic acid composition ratio (mol %) is preferably about 85/15 to about 50/50, more preferably about 75/25 to about 50/50. The weight-average molecular weight of the lactic acid/glycolic acid copolymer is preferably about 8,000 to about 20,000, more preferably about 10,000 to about 20,000. Further, the degree of dispersion (weight-average molecular weight/ number-average molecular weight) of the lactic acid/ glycolic acid copolymer is about 1.2 to about 4.0, more preferably about 1.5 to about 3.5.

The lactic acid/glycolic acid copolymer used can be produced by the known methods such as those described in the above publication and the like. The copolymer is preferably one that is produced by catalyst-free dehydration polymerization. It is preferable that the lactic acid/glycolic acid copolymer (PLGA) wherein the number-average molecular weight based on terminal group quantitation and the number-average molecular weight based on GPC measurement almost agree with each other is used.

Further, two kinds of lactic acid/glycolic acid copolymers differing in composition ratio and weight-average molecular weight may be used in an admixture of given ratio. The typical example is a mixture of lactic acid/glycolic acid copolymer wherein the composition ratio of lactic acid/ glycolic acid (mol %) is about 75/25 and the weight-average molecular weight is about 10,000 and lactic acid/glycolic acid copolymer wherein the composition ratio of lactic acid/glycolic acid (mol %) is about 50/50 and the weight-average molecular weight is about 12,000. The preferred weight ratio of the mixture is about 25/75 to about 75/25.

In the present invention, zinc oxide used for preparation of PLGA-zinc oxide complex is a little water-soluble zinc compound, and is itself insoluble or slightly soluble also in an organic solvent such as dichloromethane. The co-presence of zinc oxide and PLGA in an organic solvent such as dichloromethane quite unexpectedly provides formation of PLGA-zinc oxide complex efficiently and the subsequent dissolution in the organic solvent. These operations are accomplished simply by addition of PLGA and zinc oxide in the organic solvent, and do not need a separation process of PLGA-zinc oxide complex. To the thus obtained solution of PLGA-zinc oxide complex in an organic solvent, a physiologically active polypeptide is directly added to produce MC containing the physiologically active polypeptide easily. Further, the thus obtained MC maintains the physiologically active polypeptide biologically stable, and provides a sustained-release preparation which shows a reduced initial release and an excellent sustained release.

The physiologically active polypeptide used in the present invention includes a physiologically active polypeptide having molecular weight of preferably about 1,000 to about 50,000, more preferably about 5,000 to about 40,000.

The representative activity of the physiologically active polypeptide is hormonal activity. The physiologically active polypeptide may be natural products, synthetic products, semi-synthetic products, and their derivatives and analogues. The mode of action of the physiologically active polypeptide may be agonistic or antagonistic.

The physiologically active polypeptide for use in the present invention includes peptide hormones, cytokines, peptide neurotransmitters, hematopoietic factors, various growth factors, enzymes, polypeptide antibiotics and analgesic peptides.

Examples of the peptide hormones include insulin, somatostatin, somatostatin derivative (Sandostatin; see U.S. Pat. Nos. 4,087,390, 4,093,574, 4,100,117 and 4,253,998), growth hormones (GH), sodium diuretic peptides, gastrin, prolactin, adrenocorticotropic hormone (ACTH), ACTH derivatives (e.g., ebiratide), melanocyte-stimulating hormone (MSH), thyrotropin-releasing hormone (TRH) and salts and derivatives thereof (see JP-A 121273/1975 and 116465/1977), thyroid-stimulating hormone (TSH), luteinizing hormone (LH), follicle-stimulating hormone (FSH), human chorionic gonadotropin (HCG), thymosin, motilin, vasopressin, vasopressin derivative [desmopressin, see Folia Endocrinologica Japonica, Vol. 54, No. 5, pp. 676–691 (1978)], oxytocin, calcitonin, parathyroid hormone (PTH), glucagon, secretin, pancreozymin, cholecystokinin, angiotensin, and human placental lactogen. The peptide hormones are preferably insulin and growth hormones.

The cytokines include lymphokines and monokines. The lymphokines include interferons (alpha, beta and gamma) and interleukins (IL-2, 3, 4, 5, 6, 7, 8, 9, 10, 11, 12). The monokines include interleukin-1 (IL-1), and tumor necrosis factor (TNF). The preferred cytokine is a lymphokine and, more preferred interferon. The particularly preferred cytokine is interferon-$\alpha$.

The peptide neurotransmitters include substance P, serotonin and GABA.

The hematopoietic factors include erythropoietin (EPO), colony stimulating factors (G-CSF, GM-CSF, M-CSF), thrombopoietin (TPO), platelet-derived growth factor, and megakaryocyte potentiator.

The various growth factors include basic and acidic fibroblast growth factors (FGF) and their families (e.g., EGF, TGF-$\alpha$, TGF-$\beta$, PDGF, acidic FGF, basic FGF, FGF-9), nerve growth factor (NGF) and its family (e.g., BDNF, NT-3, NT-4, CNTF, GDNF), insulin-like growth factors (e.g. IGF-1, IGF-2, etc.) and bone morphogenetic protein (BMP) and its family.

The enzymes include superoxide dismutase (SOD), urokinase, tissue plasminogen activator (TPA), asparaginase and kallikrein.

The polypeptide antibiotics include polymixin B, colistin, gramicidin and bacitracin.

The analgesic peptides include enkephalin, enkephalin derivatives (see U.S. Pat. No. 4,277,394 and EP-A 31567), endorphin, and kyotorphin.

Further, the physiologically active polypeptides include thymopoietin, dynorphin, bombesin, caerulein, thymostimulin, thymic humoral factor (THF), blood thymic factor (FTS) and derivatives thereof (see U.S. Pat. No. 4,229,438), other thymic factors [Igaku no Ayumi, Vol. 125, No. 10, pp. 835–843 (1983)], neurotensin, bradykinin, and endothelin-antagonistic peptides (see EP-A 436189, 457195 and 496452, and JP-A 94692/1991 and 130299/1991).

The particularly preferred physiologically active polypeptides include growth hormone and insulin.

In the present invention, when the physiologically active polypeptide contains a metal, the content of the metal is preferably not greater than 0.1%, more preferably not greater than 0.01%, and most preferably not greater than 0.001%. Thus, substantially metal-free physiologically active polypeptides are most suited for the present invention. Crystalline insulin, for instance, usually contains small amounts of heavy metals such as zinc, nickel, cobalt and cadmium. Insulin containing 0.4% (w/w) zinc exists as a stable hexamer and appears to be relatively inert in the interaction with the biodegradable polymer metal salt.

If necessary, the metals occurring in the physiologically active polypeptide may be previously removed. As the method of removing the metals, known methods are employed. For example, dialyzing an acidic aqueous hydrochloric acid solution of insulin against water or an aqueous solution of ammonium acetate and lyophilizing the dialysate provide amorphous insulin with minimal metal content.

Growth hormone may be derived from any species, and it is preferably one derived from human beings. Further, although natural products extracted from the pituitary gland can be used for the present invention, genetic recombinant type GH (JP-B 12996/1994, 48987/1994) is preferred. The recombinant type human GH having the same structure with a natural type without methionine at the N-terminal group is more preferred. Such GH may be in the form of a metal salt, and one containing substantially no metal is also used.

The organic solvent used in the present invention preferably has a boiling point not exceeding 120° C. Such organic solvent includes halogenated hydrocarbons (e.g., dichloromethane, chloroform, carbon tetrachloride, etc.), alcohols (e.g. ethanol, methanol, 1,4-butanediol, 1,5-pentanediol, etc.), ethyl acetate, acetonitrile, and so on. These solvents can also be used as a mixture in a given ratio. The preferred organic solvent used singly includes, for instance, dichloromethane and acetonitrile.

The preferred organic solvent used as a mixture includes, for instance, combination of halogenated hydrocarbons (e.g., dichloromethane, chloroform) and alcohols (e.g., ethanol, methanol, 1,4-butanediol, 1,5-pentanediol) or acetonitrile. Especially, combination of dichloromethane and acetonitrile is used widely. The mixing ratio (volume ratio) of halogenated hydrocarbons relative to alcohols or acetonitrile ranges from about 40:1 to about 1:1, preferably from about 20:1 to about 1:1. Especially, single use of halogenated hydrocarbons such as dichloromethane is preferred.

In the present invention, zinc oxide used for production of a sustained-release preparation is preferably in a fine powder state. Although the reaction time is expected to become shorter as the diameter is smaller, problems of handling arise at the same time since fryability increases. The particle diameter of zinc oxide is usually about 0.001 $\mu$m to about 10 $\mu$m, preferably about 0.005 $\mu$m to about 1 $\mu$m, more preferably about 0.01 $\mu$m to about 0.1 $\mu$m.

In a solution of a biodegradable polymer and zinc oxide in an organic solvent, the content of zinc (Zn) by weight ratio relative to the biodegradable polymer is preferably about 0.001 to about 2% (w/w), more preferably about 0.01 to about 2% (w/w), most preferably about 0.1 to about 2% (w/w). The content of zinc in the solution of the biodegradable polymer and zinc oxide in the organic solvent is determined by commonly known analytical methods such as the atomic absorption analysis.

In the present specification, the sustained-release preparation is not limited as long as it is in the form of fine particles comprising a physiologically active polypeptide and a microcapsule base (i.e., a biodegradable polymer-zinc oxide complex). Examples of the fine particles include microcapsules containing one drug core in each particles, multiple-core microcapsules containing a large number of drug cores in each particles, microspheres in which a drug in a molecular form is dissolved or dispersed in the microcapsule base.

The sustained-release preparation in the present invention is produced by dispersing a physiologically active polypeptide into a solution of a biodegradable polymer and zinc oxide in an organic solvent, and then removing the organic solvent. In the present specification, a product which is produced from a biodegradable polymer and zinc oxide, and formed in a clear solution wherein the biodegradable polymer and zinc oxide are dissolved in the organic solvent is referred to as "a biodegradable polymer-zinc oxide complex".

The biodegradable polymer-zinc oxide complex may be a compound resulting from intermolecular interaction such as normal salts, complex salts, double salts and organic metal compounds, or a composition.

The biodegradable polymer-zinc oxide complex has properties such as dissolution in an organic solvent and provision of an excellent sustainability to the sustained-release preparation as a final product. Further, the complex in which a biodegradable polymer is PLGA is referred to as "a PLGA-zinc oxide complex".

In the present specification, "dispersion" means homogeneous dispersion of a physiologically active polypeptide in an organic solvent. Both solution and suspension of the physiologically active polypeptide in the organic solvent are included in the dispersion of the present invention.

In the method of the present invention, methods of removing the organic solvent include, for instance, (a) in-water drying method (o/w method), (b) phase separation method (coacervation method), (c) spray-drying method, and modifications thereof.

Hereafter, production method when microcapsules are produced as a sutained-release preparation is described.

In the method of the present invention, a biodegradable polymer and zinc oxide are first allowed to exist together in an organic solvent to prepare a solution of a biodegradable polymer-zinc oxide complex in the organic solvent. Although the concentration of the biodegradable polymer in the solution varies depending on the molecular weight and the kinds of the organic solvent, it is, for instance, about 0.1 to about 80% (w/w), preferably about 1 to about 70% (w/w), more preferably about 2 to about 60% (w/w). The amount of zinc oxide added varies depending on the kinds of the organic solvent, and is, for instance, about 0.001 to about 5% (w/w), preferably about 0.01 to about 2.5% (w/w), more preferably about 0.1 to about 2.5% (w/w), based on the amount of the biodegradable polymer.

Regarding the order of addition of the biodegradable polymer and zinc oxide to the organic solvent, zinc oxide both in a powder state or in a dispersed state in the organic solvent can be added to a solution of the biodegradable polymer in the organic solvent, conversely, a solution of the biodegradable polymer in the organic solvent can be added to a dispersion of zinc oxide in the organic solvent. Further, the organic solvent can be added after the biodegradable polymer and zinc oxide both in a powder state are admixed.

The conditions to produce a solution of a biodegradable polymer-zinc oxide complex such as PLGA-zinc oxide complex from a biodegradable polymer and zinc oxide can be changed according to the kinds of the biodegradable polymer used, the particle diameter of zinc oxide, the kinds of the organic solvent, these compositions. For instance, when PLGA is employed as a polymer, PLGA-zinc oxide complex can be obtained by the reaction usually at about 0 to about 30° C., preferably about 2 to about 25° C., for about 1 to about 168 hours, preferably about 12 to about 96 hours, more preferably about 24 to about 72 hours. However, the reaction time is not limited to the above ranges and can be determined using as an index liquid state observations by the naked eye. The produciton of PLGA-zinc oxide complex in the present invention can be confirmed by the naked eye since zinc oxide which is in a dispersed state at the time of addition dissolves in the organic solvent to give a clear solution.

Although this reaction proceeds simply by the co-presence of PLGA and zinc oxide in the organic solvent, the reaction carried out under stirring or shaking by means of suitable stirring or shaking means is advantageous to reduction of the reaction time. Further, the reaction carried out under ultrasonication is equally preferred. As the reaction temperature becomes higher, the reaction time becomes shorter. While the higher reaction temperature is at the same time accompanied with the faster degradation of PLGA.

The thus obtained biodegradable polymer-zinc oxide complex is applied to the next process preferably as a solution in an organic solvent, if necessary as a solid after removal of the organic solvent.

Then, a physiologically active polypeptide preferably in a powder state is added for dissolution or dispersion in an amount of about 0.1 to about 50% (w/w), preferably about 1 to about 20% (w/w), more preferably about 3 to about 15% (w/w), to the solution of the biodegradable polymer and zinc oxide in the organic solvent to produce a dispersion of the biodegradable polymer, zinc oxide and the physiologically active polypeptide in an organic solvent (hereafter simply referred to as a physiologically active polypeptide dispersion).

If the physiologically active polypeptide has properties such as no dissolution in the solution of the biodegradable polymer and zinc oxide in the organic solvent, turbidity by addition in a powder state, and hardness to be dispersed, it is preferred that the physiologically active polypeptide is previously dispersed in the organic solvent. To the organic solvent solution, stabilizers for the physiologically active polypeptide (e.g., serum albumin, gelatin, protamine sulfate) can be added.

For the purpose of homogeneous dispersion of the physiologically active polypeptide in the organic solvent, addition of external physical energy is preferred. Such methods include, for instance, ultrasonication, turbine-type stirrer and homogenizer. In this case, the particle size of the physiologically active polypeptide in the organic solvent is about 0.01 to about 200 $\mu$m, preferably about 0.05 to about 100 $\mu$m, more preferably about 0.1 to about 50 $\mu$m. The concentration of the physiologically active polypeptide in the organic solvent is about 1 to about 50%, preferably about 2 to about 20%. Such treatment provides uniformity in the particle size of the physiologically active polypeptide in the organic solvent, and homogeneous dispersion in a solution of the biodegradable polymer and zinc oxide in the organic solvent.

Further, the physiologically active polypeptide can be previously dispersed in the organic solvent independently of the biodegradable polymer-zinc oxide complex. In this case, the composition of the organic solvent used and that of the organic solvent used for dissolution of the biodegradable polymer and zinc oxide may be the same or different from each other. For instance, it is possible that the biodegradable polymer-zinc oxide complex is dissolved in dichloromethane, the physiologically active polypeptide is dispersed in acetonitrile, and then both are admixed. In this case, the ratio (volume ratio) of the physiologically active polypeptide to the biodegradable polymer-zinc oxide complex is, for instance, about 1:1,000 to about 1:1, preferably about 1:200 to about 1:5, especially preferably about 1:100 to about 1:5.

(a) In-water drying method (o/w method)

The dispersion of the physiologically active polypeptide prepared in the above manner is further added to an aqueous phase to form an o/w emulsion. Then the solvent in the oil phase is volatilized to produce microcapsules. In this case, an emulsifier may be added to the external aqueous phase. The emulsifier may be any substance capable of providing for a stable o/w emulsion. Examples of such emulsifiers include anionic surfactants, nonionic surfactants, polyoxyethylene-castor oil derivatives, polyvinylpyrrolidone, polyvinyl alcohol, carboxymethylcellulose, lecithin, gelatin, hyaluronic acid and so on. The preferred emulsifier is polyvinyl alcohol. These emulsifiers may be used singly or in combination of two or more. The concentration of the emulsifier in the external aqueous phase ranges from about 0.001 to about 20% (w/w), preferably from about 0.01 to about 10% (w/w), especially preferably from about 0.05 to about 5% (w/w).

The thus obtained microcapsules are recovered by centrifugation or filtration, washed with distilled water to remove the emulsifier etc. adhering to the surface of microcapsules, redispersed in distilled water, and lyophilized.

Then, if necessary, water and the organic solvent in the microcapsules are further removed by heating. The heating may be conducted under reduced pressure. Regarding the heating conditions, heating and drying are conducted at a temperature not lower than a glass transition temperature of the biodegradable polymer and not so high as to cause aggregation of each microcapsule particle. The heating and drying are conducted preferably at a temperature ranging from the glass transition temperature of the biodegradable polymer to a temperature which is about 30° C. higher than the glass transition temperature. The glass transition temperature is defined as the intermediate glass transition point obtained using a differential scanning calorimeter when the temperature is increased at a rate of 10 to 20° C. per minute.

(b) Phase separation method (Coacervation method)

When MC is produced by the present method, a coacervating agent is gradually added to the above described dispersion of the physiologically active polypeptide under stirring to precipitate and solidify MC. The amount of the coacervating agent used is about 0.01 to about 1,000 times by volume, preferably about 0.05 to about 500 times by volume, especially preferably about 0.1 to about 200 times by volume. Any coacervating agent can be used, as long as it is a polymeric, mineral oil or vegetable oil compound miscible with the organic solvent for dissolution of a biodegradable polymer and it does not dissolve the biodegradable polymer used. Specifically, examples of such coacervating agents include silicone oil, sesame oil, soybean oil, corn oil, cottonseed oil, coconut oil, linseed oil, mineral oil, n-hexane and n-heptane. Two or more of these may be used in combination.

The thus obtained MC are recovered by filtration, washed repeatedly with heptane etc. to remove the coacervating agent. Further, washing is conducted in the same manner as in the above (a), followed by lyophilization.

In the production of MC by the in-water drying method or coacervation method, an antiaggregation agent may be added in the process of washing MC for preventing aggregation of particles. Examples of the antiaggregation agent include, for instance, water-soluble polysaccharides such as mannitol, lactose, glucose, starches (e.g., corn starch), hyaluronic acid and its alakaline metal salt; amino acids such as glycine and alanine; proteins such as fibrin and collagen; and inorganic salts such as sodium chloride and sodium hydrogen phosphate, and so on.

(c) Spray-drying method

When MC is produced by the present method, the dispersion of the physiologically active polypeptide is sprayed via a nozzle into the drying chamber of a spray drier to volatilize the organic solvent in the fine droplets in a very short time to yield MC. Examples of the nozzle include, for instance, a two-fluid nozzle type, a pressure nozzle type and a rotary disc type. It is also advantageous, if necessary, to spray an aqueous solution of the above-described antiaggregation agent via another nozzle in order to prevent aggregation of each MC particle.

The thus obtained MC is washed in the same manner as in the above (a), if necessary followed by heating (if necessary under reduced pressure) to remove water and the organic solvent.

In the present invention, the entrapment ratio of the physiologically active polypeptide such as GH into MC is preferably at least 50% when PLGA-zinc oxide complex is employed as a microcapsule base.

The contents of the physiologically active polypeptide in the sustained-release preparation of the present invention are, for instance, about 0.1 to about 30% (w/w), preferably about 0.2 to about 20% (w/w), more preferably about 0.5 to about 10% (w/w).

The sustained-release preparation of the present invention can be administered, for instance, as fine particles such as microcapsules as such, or in the form of various dosage forms of non-oral preparations (e.g., intramuscular, subcutaneous or visceral injections; indwellable preparations; nasal, rectal or uterine transmucosal preparations etc.) or oral preparations (e.g., capsules such as hard capsules and soft capsules etc.; solid preparations such as granules and powders etc.; liquid preparations such as suspensions etc.) by using the fine particles as a raw material.

The preparations of these dosage forms can be produced by known methods in common use for pharmaceutical production.

The sustained-release preparation of the present invention is preferably in the form of injections. To prepare injections using the fine particles such as microcapsules obtained by the above methods, the fine particles may be formulated with a dispersant (e.g., surfactants such as Tween 80, HCO-60; polysaccharides such as carboxymethylcellulose, sodium alginate, sodium hyaluronate; protamine sulfate; polyethylene glycol 400, etc.), a preservative (e.g., methyl paraben, propyl paraben, etc.), an isotonizing agent (e.g., sodium chloride, mannitol, sorbitol, glucose, etc.), and a local anesthetic (e.g., xylocaine hydrochloride, chlorobutanol, etc.), to provide an aqueous suspension, or dispersed with vegetable oil (e.g., sesame oil, corn oil, etc.), or a mixture thereof with a phospholipid (e.g., lecithin) or medium-chain fatty acid triglycerides (e.g., Miglyol 812) to provide an oily suspension.

The sustained-release preparation is especially preferably in the form of fine particles. The particle diameter of the sustained-release preparation for an injectable suspension may be selected from the range satisfying the requirements for the degree of dispersion and the needle passability for the injection. For instance, the particle diameter is within the range of about 0.1 to about 300 $\mu$m, preferably about 1 to about 150 $\mu$m, more preferably about 2 to about 100 $\mu$m, as the mean particle diameter.

Methods of preparing the above fine particles as a sterile preparation include, but are not limited to, the method in which the entire production process is sterile, the method in which the gamma rays are used as the sterilant, and the method in which an antiseptic is added during the manufacturing process.

The sustained-release preparation can be safely used in mammals (e.g., humans, bovine, swine, dogs, cats, mice, rats, rabbits, etc.) with low toxicity.

Indication of the sustained-release preparation varies depending on the physiologically active polypeptide used. The sustained-release preparation is useful to prevent or treat diabetes when insulin is used as the physiologically active polypeptide; viral hepatitis (e.g., type C hepatitis, HBe antigen-positive active hepatitis) and cancer (e.g., renal carcinoma, multiple myeloma, etc.) when interferon-a is used; anemia (e.g., anemia during dialysis of kidney) when erythropoietin is used; neutropenia (e.g., in cancer therapy) and infections when G-CSF is used; cancer (e.g., hemangioendothelioma) when IL-2 is used; fracture, wound (e.g., bedsore), periodontitis and gastrointestinal ulcer when FGF is used; thrombocytopenia when FGF-9 is used; senile dementia and neuropathy when NGF is used; thrombosis when TPA is used; and cancer when tumor necrosis factor is used.

Further, the sustained-release preparation containing GH is applied to Turner's syndrome, chronic renal diseases, achondroplasia, and adult hypopituitarism as well as pituitary dwarfism, based on growth hormone action of GH. Further, GH is reported to be applied to diseases such as Down syndrome, Silver syndrome, hypochondroplasia and juvenile chronic arthritis to provide excellent therapeutic effects.

Although varing depending on the kinds and contents of the physiologically active polypeptide, duration of the release, target disease, subject animal species and other factors, the dose of the sustained-release preparation may be set at any level, as long as the effective concentration of the physiologically active polypeptide in the body is maintained.

For instance, when the sustained-release preparation is one designed for one week release, the dose of the physiologically active polypeptide can be chosen from the range of preferably about 0.0001 to about 10 mg/kg body weight, more preferably about 0.0005 to about 1 mg/kg body weight, per an adult. The preferred administration frequency of the sustained-release preparation can be suitably chosen from once a week, once every two weeks and etc. depending on the kinds and contents of the physiologically active polypeptide, the dosage form, duration of the release, target disease, subject animal species and other factors.

When the physiologically active polypeptide as an active ingredient in the sustained-release preparation is, for instance, insulin, the dose per administration to an diabetic adult is chosen from the range of usually about 0.001 to about 1 mg/kg body weight, preferably about 0.01 to about 0.2 mg/kg body weight, as an effective ingredient. And the preferred administration frequency is once a week.

When the physiologically active polypeptide as an active ingredient in the sustained-release preparation is GH, the dose may be set at any level, as long as the effective concentration of GH in the body is maintained, although varing depending on the kinds and contents of GH, duration of the release, target disease, subject animal species and other factors. Regarding the treatment of the above described diseases, when the sustained-release preparation is one designed for two week release, the dose of GH can be chosen from the range of about 0.01 to about 5 mg/kg body weight, more preferably about 0.05 to about 1 mg/kg body weight, per a child or an adult for safe administration. The preferred administration frequency can be suitably chosen from once a week, once every two weeks, once a month and etc., depending on the contents of GH, the dosage form, duration of the release, target disease, subject animal species and other factors.

The sustained-release preparation is preferably stored at ordinary temperature or in cold place. More preferably, the sustained-release preparation is stored in cold place. The "ordinary temperature" and the "cold place" are defined in the pharmacopoeia of Japan. Namely, the "ordinary temperature" means 15 to 25° C., and the "cold place" means a temperature not exceeding 15° C.

BEST MODE FOR CARRYING OUT THE INVENTION

The present invention is hereafter described in more detail by means of the following Working Examples and Experimental Examples, which are not to be construed to limit the scope of the present invention.

WORKING EXAMPLE 1

1 g of lactic acid/glycolic acid copolymer (lactic acid/glycolic acid=50/50(mol %), weight-average molecular weight 10,000) and 6.6 mg of zinc oxide were added to 1.7 ml of dichloromethane, which was stirred (60 rpm) at 25° C. for 3 days to yield a clear solution of lactic acid/glycolic acid copolymer-zinc oxide complex in an organic solvent. To this solution was added 53.0 mg of a freeze-dried powder of human growth hormone, and they were admixed by means of a voltex mixer and a small-size homogenizer. Then, an ultrasonication was carried out to yield a solution of human growth hormone and lactic acid/glycolic acid copolymer-zinc oxide complex in an organic solvent. This organic solvent solution was poured into 400 ml of a 0.1% (w/v) polyvinyl alcohol (PVA) aqueous solution previously adjusted at 18° C., followed by emulsification with a turbine-type homomixer to yield an o/w emulsion. This o/w emulsion was stirred at room temperature to volatilize dichloromethane. The obtained microcapsules were collected by centrifugation (about 1,500 rpm). The obtained precipitate was washed twice with 400 ml of distilled water, which was freeze-dried to yield 521 mg of powdery microcapsules containing human growth hormone.

WORKING EXAMPLE 2

1 g of lactic acid/glycolic acid copolymer (lactic acid/glycolic acid=50/50(mol %), weight-average molecular weight 10,000) and 13.1 mg of zinc oxide were dissolved in 2.3 ml of dichloromethane to yield a solution of lactic acid/glycolic acid copolymer-zinc oxide complex in an organic solvent. To this solution was added 53.3 mg of a freeze-dried powder of human growth hormone, which was treated in the same manner as in Working Example 1 to yield 536 mg of powdery microcapsules containing human growth hormone.

WORKING EXAMPLE 3

1 g of lactic acid/glycolic acid copolymer (lactic acid/glycolic acid=50/50(mol %), weight-average molecular weight 10,000) and 21.9 mg of zinc oxide were dissolved in 2.8 ml of dichloromethane to yield a solution of lactic acid/glycolic acid copolymer-zinc oxide complex in an organic solvent. To this solution was added 53.8 mg of a freeze-dried powder of human growth hormone, which was treated in the same manner as in Working Example 1 to yield 589 mg of powdery microcapsules containing human growth hormone.

WORKING EXAMPLE 4

1 g of lactic acid/glycolic acid copolymer (lactic acid/glycolic acid=50/50(mol %), weight-average molecular weight 12,000) and 5.1 mg of zinc oxide were dissolved in 1.9 ml of dichloromethane to yield a solution of lactic acid/glycolic acid copolymer-zinc oxide complex in an organic solvent. To this solution was added 52.9 mg of a freeze-dried powder of human growth hormone, which was treated in the same manner as in Working Example 1 to yield 506 mg of powdery microcapsules containing human growth hormone.

WORKING EXAMPLE 5

1 g of lactic acid/glycolic acid copolymer (lactic acid/glycolic acid=50/50(mol %), weight-average molecular weight 12,000) and 10.2 mg of zinc oxide were dissolved in 2.5 ml of dichloromethane to yield a solution of lactic acid/glycolic acid copolymer-zinc oxide complex in an organic solvent. To this solution was added 53.2 mg of a freeze-dried powder of human growth hormone, which was treated in the same manner as in Working Example 1 to yield 568 mg of powdery microcapsules containing human growth hormone.

WORKING EXAMPLE 6

1 g of lactic acid/glycolic acid copolymer (lactic acid/glycolic acid=65/35(mol %), weight-average molecular weight 12,000) and 17.0 mg of zinc oxide were dissolved in 3.0 ml of dichloromethane to yield a solution of lactic acid/glycolic acid copolymer-zinc oxide complex in an organic solvent. To this solution was added 53.5 mg of a freeze-dried powder of human growth hormone, which was treated in the same manner as in Working Example 1 to yield 561 mg of powdery microcapsules containing human growth hormone.

WORKING EXAMPLE 7

1 g of lactic acid/glycolic acid copolymer (lactic acid/glycolic acid=50/50(mol %), weight-average molecular weight 15,000) and 4.5 mg of zinc oxide were dissolved in 2.0 ml of dichloromethane to yield a solution of lactic acid/glycolic acid copolymer-zinc oxide complex in an organic solvent. To this solution was added 52.9 mg of a freeze-dried powder of human growth hormone, which was treated in the same manner as in Working Example 1 to yield 540 mg of powdery microcapsules containing human growth hormone.

WORKING EXAMPLE 8

1 g of lactic acid/glycolic acid copolymer (lactic acid/glycolic acid=50/50(mol %), weight-average molecular weight 15,000) and 8.9 mg of zinc oxide were dissolved in 2.6 ml of dichloromethane to yield a solution of lactic acid/glycolic acid copolymer-zinc oxide complex in an organic solvent. To this solution was added 53.1 mg of a freeze-dried powder of human growth hormone, which was treated in the same manner as in Working Example 1 to yield 559 mg of powdery microcapsules containing human growth hormone.

WORKING EXAMPLE 9

1 g of lactic acid/glycolic acid copolymer (lactic acid/glycolic acid=50/50(mol %), weight-average molecular weight 15,000) and 14.9 mg of zinc oxide were dissolved in 3.1 ml of dichloromethane to yield a solution of lactic acid/glycolic acid copolymer-zinc oxide complex in an organic solvent. To this solution was added 53.4 mg of a freeze-dried powder of human growth hormone, which was treated in the same manner as in Working Example 1 to yield 464 mg of powdery microcapsules containing human growth hormone.

WORKING EXAMPLE 10

1 g of lactic acid/glycolic acid copolymer (lactic acid/glycolic acid=50/50(mol %), weight-average molecular weight 20,000) and 4.0 mg of zinc oxide were dissolved in 2.5 ml of dichloromethane to yield a solution of lactic acid/glycolic acid copolymer-zinc oxide complex in an organic solvent. To this solution was added 52.8 mg of a freeze-dried powder of human growth hormone, which was treated in the same manner as in Working Example 1 to yield 595 mg of powdery microcapsules containing human growth hormone.

WORKING EXAMPLE 11

1 g of lactic acid/glycolic acid copolymer (lactic acid/glycolic acid=50/50(mol %), weight-average molecular weight 20,000) and 7.9 mg of zinc oxide were dissolved in 3.6 ml of dichloromethane to yield a solution of lactic acid/glycolic acid copolymer-zinc oxide complex in an organic solvent. To this solution was added 53.1 mg of a freeze-dried powder of human growth hormone, which was treated in the same manner as in Working Example 1 to yield 478 mg of powdery microcapsules containing human growth hormone.

WORKING EXAMPLE 12

1 g of lactic acid/glycolic acid copolymer (lactic acid/glycolic acid=50/50(mol %), weight-average molecular weight 20,000) and 13.2 mg of zinc oxide were dissolved in 5.2 ml of dichloromethane to yield a solution of lactic acid/glycolic acid copolymer-zinc oxide complex in an organic solvent. To this solution was added 53.3 mg of a freeze-dried powder of human growth hormone, which was treated in the same manner as in Working Example 1 to yield 534 mg of powdery microcapsules containing human growth hormone.

WORKING EXAMPLE 13

1 g of lactic acid/glycolic acid copolymer (lactic acid/glycolic acid=75/25(mol %), weight-average molecular weight 10,500) and 6.6 mg of zinc oxide were dissolved in 3.0 ml of dichloromethane to yield a solution of lactic acid/glycolic acid copolymer-zinc oxide complex in an organic solvent. To this solution was added 53.0 mg of a freeze-dried powder of human growth hormone, which was treated in the same manner as in Working Example 1 to yield 521 mg of powdery microcapsules containing human growth hormone.

WORKING EXAMPLE 14

1 g of lactic acid/glycolic acid copolymer (lactic acid/glycolic acid=85/15(mol %), weight-average molecular weight 12,000) and 5.8 mg of zinc oxide were dissolved in 2.0 ml of dichloromethane to yield a solution of lactic acid/glycolic acid copolymer-zinc oxide complex in an organic solvent. To this solution was added 53.0 mg of a freeze-dried powder of human growth hormone, which was treated in the same manner as in Working Example 1 to yield 503 mg of powdery microcapsules containing human growth hormone.

WORKING EXAMPLE 15

1.89 g of lactic acid/glycolic acid copolymer (lactic acid/glycolic acid=50/50(mol %), weight-average molecular weight 10,000) and 10 mg of zinc oxide were dissolved in 3.4 ml of dichloromethane to yield a solution of lactic acid/glycolic acid copolymer-zinc oxide complex in an organic solvent. To this solution was added 100 mg of a freeze-dried powder of human growth hormone, which was treated in the same manner as in Working Example 1 to yield 1.41 g of powdery microcapsules containing human growth hormone.

WORKING EXAMPLE 16

1.89 g of lactic acid/glycolic acid copolymer (lactic acid/glycolic acid=50/50(mol %), weight-average molecular weight 12,000) and 10 mg of zinc oxide were dissolved in 3.5 ml of dichloromethane to yield a solution of lactic acid/glycolic acid copolymer-zinc oxide complex in an organic solvent. To this solution was added 100 mg of a freeze-dried powder of human growth hormone, which was treated in the same manner as in Working Example 1 to yield 1.41 g of powdery microcapsules containing human growth hormone.

WORKING EXAMPLE 17

1.89 g of lactic acid/glycolic acid copolymer (lactic acid/glycolic acid=50/50(mol %), weight-average molecular weight 14,000) and 10 mg of zinc oxide were dissolved in 4.0 ml of dichloromethane to yield a solution of lactic acid/glycolic acid copolymer-zinc oxide complex in an organic solvent. To this solution was added 100 mg of a freeze-dried powder of human growth hormone, which was treated in the same manner as in Working Example 1 to yield 1.40 g of powdery microcapsules containing human growth hormone.

WORKING EXAMPLE 18

1.89 g of lactic acid/glycolic acid copolymer (lactic acid/glycolic acid=50/50(mol %), weight-average molecular weight 16,000) and 10 mg of zinc oxide were dissolved in 4.2 ml of dichloromethane to yield a solution of lactic acid/glycolic acid copolymer-zinc oxide complex in an organic solvent. To this solution was added 100 mg of a freeze-dried powder of human growth hormone, which was treated in the same manner as in Working Example 1 to yield 1.34 g of powdery microcapsules containing human growth hormone.

COMPARATIVE EXAMPLE 1

Lactic acid/glycolic acid copolymer (lactic acid/glycolic acid=50/50(mol %), weight-average molecular weight 15,000) was dissolved in dichloromethane (950 mg/ml) to yield a solution of lactic acid/glycolic acid copolymer in an organic solvent. 1 ml of this solution and 1 ml of a solution of a freeze-dried powder of human growth hormone in dichloromethane (50 mg/ml) were mixed, which was treated in the same manner as in Working Example 1 to yield 490 mg of powdery microcapsules containing human growth hormone.

COMPARATIVE EXAMPLE 2

1.90 g of lactic acid/glycolic acid copolymer (lactic acid/glycolic acid=50/50(mol %), weight-average molecular weight 10,000) was dissolved in 2.6 ml of dichloromethane to yield a solution of lactic acid/glycolic acid copolymer in an organic solvent. To this solution was added 100 mg of a freeze-dried powder of human growth hormone, which was treated in the same manner as in Working Example 1 to yield 1.28 g of powdery microcapsules containing human growth hormone.

COMPARATIVE EXAMPLE 3

1.90 g of lactic acid/glycolic acid copolymer (lactic acid/glycolic acid=50/50(mol %), weight-average molecular weight 12,000) was dissolved in 2.8 ml of dichloromethane to yield a solution of lactic acid/glycolic acid copolymer in an organic solvent. To this solution was added 100 mg of a freeze-dried powder of human growth hormone, which was treated in the same manner as in Working Example 1 to yield 1.18 g of powdery microcapsules containing human growth hormone.

COMPARATIVE EXAMPLE 4

1.90 g of lactic acid/glycolic acid copolymer (lactic acid/glycolic acid=50/50(mol %), weight-average molecular weight 14,000) was dissolved in 3.0 ml of dichloromethane to yield a solution of lactic acid/glycolic acid copolymer in an organic solvent. To this solution was added 100 mg of a freeze-dried powder of human growth hormone, which was treated in the same manner as in Working Example 1 to yield 0.89 g of powdery microcapsules containing human growth hormone.

COMPARATIVE EXAMPLE 5

1.90 g of lactic acid/glycolic acid copolymer (lactic acid/glycolic acid=50/50(mol %), weight-average molecular weight 16,000) was dissolved in 3.2 ml of dichloromethane to yield a solution of lactic acid/glycolic acid copolymer in an organic solvent. To this solution was added 100 mg of a freeze-dried powder of human growth hormone, which was treated in the same manner as in Working Example 1 to yield 1.26 g of powdery microcapsules containing human growth hormone.

EXPERIMENTAL EXAMPLE 1

308 mg of microcapsules containing human growth hormone and PLGA-zinc oxide complex obtained in Working Example 7; 351 mg of microcapsules containing human growth hormone and PLGA-zinc oxide complex obtained in Working Example 8; 327 mg of microcapsules containing human growth hormone and PLGA-zinc oxide complex obtained in Working Example 9; and 229 mg of microcapsules containing human growth hormone and PLGA obtained in Comparative Example 1; were dispersed in respectively 2.25 ml of dispersion medium (composition of the dispersion medium: mannitol (5%), carboxymethylcellulose (0.5%) and Tween 20 (0.1%) were dissolved in distilled water, followed by adjustment of pH to 6.0 with acetic acid) (the same shall apply hereinafter), 2.25 ml of dispersion medium, 1.75 ml of dispersion medium, and 1.75 ml of dispersion medium.

0.5 ml of the thus obtained dispersion (containing 3 mg of human GH) was subcutaneously administered at the back of rats under anesthesia with ether. Blood was collected via tail vein with the passage of time and blood serum was separated. The human GH concentration in the obtained blood serum was determined by means of a radioimmunoassay (Ab Beads HGH, produced by Eiken Kagaku, Japan). The obtained results are shown in Table 1.

TABLE 1

| Sustained-release preparation containing growth hormone | Blood Concentration (ng/ml) | | | | | | |
|---|---|---|---|---|---|---|---|
| | 1st day | 2nd day | 4th day | 6th day | 7th day | 9th day | 11th day |
| Working Ex. 7 | 16.7 | 8.6 | 8.4 | 14.8 | 26.6 | 13.5 | 2.8 |
| Working Ex. 8 | 17.9 | 10.6 | 14.1 | 22.5 | 27.8 | 15.9 | 3.5 |
| Working Ex. 9 | 14.0 | 8.5 | 15.8 | 33.9 | 28.2 | 17.8 | 7.7 |
| Comparative Ex. 1 | 4.3 | 1.7 | 2.1 | 3.1 | 5.0 | 8.0 | 2.7 |

The human GH concentration in groups in which microcapsules containing human growth hormone and PLGA-zinc oxide complex obtained in Working Examples 7, 8 and 9 were administered showed significantly high values compared with that in a group in which microcapsules containing human growth hormone and PLGA obtained in Comparative Example 1 were administered, and further showed a long-term sustained-release. According to the method of the present invention, a sustained-release preparation with an excellent release profile can be produced.

EXPERIMENTAL EXAMPLE 2

550 mg, 556 mg, 576 mg and 573 mg of microcapsules containing human growth hormone and PLGA-zinc oxide complex respectively obtained in Working Examples 15, 16, 17 and 18 were dispersed in 3.38 ml of the dispersion medium described in Experimental Example 1. While 548 mg, 548 mg, 567 mg and 560 mg of microcapsules containing human growth hormone and PLGA obtained in Comparative Examples 2, 3, 4 and 5 were dispersed in 3.38 ml of the same dispersion medium.

0.75 ml of the thus obtained dispersion (containing 6 mg of human GH) was subcutaneously administered at the back of rats under anesthesia with ether. Blood was collected via tail vein with the passage of time and blood serum was separated. The human GH concentration in the obtained blood serum was determined by means of the radioimmunoassay described in Experimental Example 1. The obtained results are shown in Tables 2 to 5.

TABLE 2

| Sustained-release preparation containing growth hormone | Blood Concentration (ng/ml) | | | |
|---|---|---|---|---|
| | 4th day | 7th day | 9th day | 11th day |
| Working Ex. 15 | 24.8 | 24.5 | 15.2 | 6.3 |
| Comparative Ex. 2 | 13.8 | 8.1 | 5.1 | 3.9 |

TABLE 3

| Sustained-release preparation containing growth hormone | Blood Concentration (ng/ml) | | | |
|---|---|---|---|---|
| | 4th day | 7th day | 9th day | 11th day |
| Working Ex. 16 | 24.6 | 25.3 | 16.3 | 8.7 |
| Comparative Ex. 3 | 9.2 | 10.1 | 9.6 | 6.8 |

TABLE 4

| Sustained-release preparation containing growth hormone | Blood Concentration (ng/ml) | | | |
|---|---|---|---|---|
| | 4th day | 7th day | 9th day | 11th day |
| Working Ex. 17 | 12.5 | 35.4 | 29.5 | 9.7 |
| Comparative Ex. 4 | 7.6 | 14.8 | 7.7 | 6.2 |

TABLE 5

| Sustained-release preparation containing growth hormone | Blood Concentration (ng/ml) | | | |
|---|---|---|---|---|
| | 4th day | 7th day | 9th day | 11th day |
| Working Ex. 18 | 11.8 | 31.8 | 35.5 | 11.3 |
| Comparative Ex. 5 | 4.9 | 13.8 | 18.5 | 6.7 |

The human GH concentration in groups in which microcapsules containing human growth hormone and PLGA-zinc oxide complex obtained in Working Examples 15, 16, 17 and 18 were administered showed significantly high values compared with that in groups in which microcapsules containing human growth hormone and PLGA obtained in Comparative Examples 2, 3, 4 and 5 were administered.

Industrial Applicability

According to the present invention, a sustained-release preparation which shows a high entrapment ratio of a physiologically active polypeptide such as growth hormone and its constant high blood concentration levels over a long period of time can be provided.

What is claimed is:

1. A method of producing a sustained-release preparation which comprises dispersing a physiologically active polypeptide into a solution of a lactic acid/glycolic acid copolymer, wherein a molecular composition ratio of lactic acid/glycolic acid in the acid/glycolic acid copolymer is about 85/15 to about 50/50 and zinc oxide in an organic solvent, followed by removing the organic solvent.

2. The method according to claim 1, wherein the physiologically active polypeptide is growth hormone.

3. The method according to claim 1, wherein the weight-average molecular weight of the lactic acid/glycolic acid copolymer is about 8,000 to about 20,000.

4. The method according to claim 1, wherein the content of zinc relative to the lactic acid/glycolic acid copolymer, wherein a molecular composition ratio of lactic acid/glycolic acid in the lactic acid/glycolic acid copolymer is about 85/15 to about 50/50 biodegradable polymer in the organic solvent solution is about 0.001 to about 2% by weight.

5. The method according to claim 1, wherein the mean particle diameter of the sustained-release preparation is about 0.1 to about 300 μm.

6. The method according to claim 1, wherein the sustained-release preparation is for injection.

7. The method according to claim 1, wherein an o/w emulsion comprising a dispersion prepared by dispersing growth hormone into a solution of lactic acid/glycolic acid copolymer and zinc oxide in an organic solvent as an oil phase is subjected to in-water drying.

8. The method according to claim 1, wherein the preparation is a microcapsule.

9. A dispersion which is prepared by dispersing a physiologically active polypeptide into a solution of lactic acid/glycolic acid copolymer and zinc oxide in an organic solvent.

10. The dispersion according to claim 9, wherein the physiologically active polypeptide is growth hormone.

11. The sustained-release preparation which is produced by the method according to claim 1.

* * * * *

UNITED STATES PATENT AND TRADEMARK OFFICE
CERTIFICATE OF CORRECTION

| | | |
|---|---|---|
| PATENT NO. | : 6,197,350 B1 | Page 1 of 1 |
| APPLICATION NO. | : 09/308971 | |
| DATED | : March 6, 2001 | |
| INVENTOR(S) | : Yutaka Yamagata, Masafumi Misaki and Susumu Iwasa | |

It is certified that error appears in the above-identified patent and that said Letters Patent is hereby corrected as shown below:

At Col. 1, line 3, after the Title of the Invention, insert

-- This application is the National Phase filing of International Patent Application PCT/JP97/04671, filed December 19, 1997. --

Signed and Sealed this

Twenty-second Day of January, 2008

JON W. DUDAS
*Director of the United States Patent and Trademark Office*